United States Patent [19]

Paszthory et al.

[11] 4,042,622
[45] Aug. 16, 1977

[54] PROCESS FOR THE PREPARATION OF N-ACETOACETYL-2,5-DIMETHOXY-4-CHLOROANILIDE

[75] Inventors: Emmerich Paszthory, Hofheim, Taunus; Ernst Hille, Rossert, Taunus; Karl-Gerhard Seifert, Frankfurt am Main; Vincenz Zimmermann, Nauheim, all of Germany

[73] Assignee: Hoechst Aktiengesellschaft, Frankfurt am Main, Germany

[21] Appl. No.: 680,670

[22] Filed: Apr. 27, 1976

[30] Foreign Application Priority Data

Apr. 29, 1975 Germany .............................. 2518984

[51] Int. Cl.$^2$ .......................................... C07C 102/00
[52] U.S. Cl. .................................................. 260/562 K
[58] Field of Search ................................... 260/562 K

[56] References Cited

U.S. PATENT DOCUMENTS

| 1,982,675 | 12/1934 | Law | 260/562 K |
| 2,152,132 | 3/1939 | Boese | 260/562 K |
| 2,174,239 | 9/1939 | Gleason | 260/562 K |
| 2,700,037 | 1/1955 | Schmid | 260/562 K |
| 2,714,117 | 7/1955 | Lacey et al. | 260/562 K |
| 2,913,495 | 11/1959 | Goldsmith | 260/562 K |
| 3,063,899 | 11/1962 | Ehrhart et al. | 260/562 K |
| 3,121,743 | 2/1964 | Branch | 260/562 K |
| 3,304,328 | 2/1967 | Pelley | 260/562 K |

FOREIGN PATENT DOCUMENTS 723,057  2/1955  United Kingdom

*Primary Examiner*—Arthur P. Demers
*Attorney, Agent, or Firm*—Curtis, Morris & Safford

[57] ABSTRACT

N-acetoacetyl-2,5-dimethoxy-4-chloroanilide is obtained in high yield and purity by suspending 2,5-dimethoxy-4-chloroaniline in water and adding the complete amount of diketene necessary altogether at the beginning of the reaction. The product is obtained in a purity allowing its use as an azoic coupling component without purification.

8 Claims, No Drawings

PROCESS FOR THE PREPARATION OF N-ACETOACETYL-2,5-DIMETHOXY-4-CHLOROANILIDE

The present invention relates to a process for the preparation of N-acetoacetyl-2,5-dimethoxy-4-chloroanilide.

N-acetoacetyl-2,5-dimethoxy-4-chloroanilide is a coupling component for the preparation of azo pigments.

It was found that N-acetoacetyl-2,5-dimethoxy-4-chloroanilide can be prepared by reacting 2,5-dimethoxy-4-chloroaniline suspended in water with diketene, the diketene being added to the reaction in total right from the beginning.

The following is a description of advantageous embodiments of the invention:

The substituted aniline is first suspended in water to which aqueous suspension an inorganic or preferably organic acid is added to accelerate the reaction. 0.1 to 1 mol of acid are advantageously added per 1 mol of aniline. To facilitate the distribution of the diketene in the reaction mixture, a surfactant may be added. Suitable surfactants are the usual emulsifiers, espcecially anionactive compounds. A thorough and rapid mixture of the reactants during the whole reaction process is also recommendable.

The diketene is advantageously added in amounts of from 1.05 to 1.5 mols per mol of aniline. When no acid is added, a relatively high excess of diketene is necessary to obtain a sufficient reaction speed, on the other hand, the acid catalysis causes a sufficient reaction speed, so that a small excess of diketene is needed for the reaction. Although the reactants do not form a homogeneous phase, surprisingly the diketene can be added to the reaction mixture in total right from the beginning.

At the beginning, the reaction temperature should be within the range of from about 0° to about 30° C, preferably about 5° C. In the course of the reaction, the temperature may rise up to about 50° C, preferably, however, a reaction temperature of 30° C is not exceeded by using a suitable mode of carrying out the reaction, for example, by cooling, because by-products may be formed at elevated temperatures.

When the reaction is completed, it is possible to stir for up to about 5 hours. Then, the precipitate is suction-filtered, washed with water and dried.

The process according to the invention permits to obtain the product in a nearly quantitative yield and with a degree of purity that makes further purification unnecessary for the preparation of azo pigments.

The following Examples illustrate the invention, the parts and percentages being by weight, unless stated otherwise:

EXAMPLE 1

In a 7 liter stainless steel vessel provided with a propeller stirrer, 0.5 kg of 2,5-dimethoxy-4-chloroaniline (in form of 833 g of 60% moist material) was stirred with 1 l of water and 5 g of an emulsifier (35% aqeous solution of a condensation product of 3 mols of nonyl phenol, 2 mols of formaldehyde, 18 mols of ethylene oxide, 3 mols of maleic acid anhydride and 3 mols of sodium sulfite; (cf. German Offenlegungsschrift No. 2,132,405, Example 7). To the aqueous suspension were added 20 g of glacial acetic acid. At 10° C 350 g of 93% diketene were added to the suspension all at once. The reaction mixture was thoroughly mixed with the propeller mixer (700 rpm). The temperature rose to 30° C. After 2 hours, the precipitate was suction-filtered, washed with water and dried. The yield was 686 g (95%).

EXAMPLE 2

In a 500 liter stainless steel vessel, 45.4 kg of 2,5-dimethoxy-4-chloroaniline (in form of 75.7 kg of a 60% moist material) were stirred with 300 l of water. The aqueous suspension was cooled at 5° C with brine and 13 kg of glacial acetic acid were added. Then, 30 kg of 97% diketene were added all at once. The reaction mixture was thoroughly mixed with a propeller mixter (700 rpm), the temperature rising to 25° C during about 50 minutes. The mixture was again cooled by means of brine, so that the temperature did not exceed 25° C. The mixture was stirred for another 3 hours and the precipitate was suction-filtered, washed with water and dried. The yield was 61.8 kg (94%).

EXAMPLE 3

In a 7.5 m$^3$ stainless steel vessel, 533 kg of 2,5-dimethoxy-4-chloroaniline (in form of 711 kg of about 75% moist material) were stirred with 3 m$^3$ of water. By cooling with brine, the suspension was cooled to 3° C, 160 kg of glacial acetice acid were added and 360 kg of 97% diketene were added all at once. The reaction mixture was stirred with a frame stirrer (60 rpm) and additionally circulated by pumping through a toothed disk mill during the reaction. The temperature rose to 15° to 20° C in the course of about 20 minutes, in which process the product began to crystallize out. As soon as the temperature exceeded 20° C, cooling prevented the temperature from rising over 25° C. After a two hours' stirring, the precipitate was centrifuged off, the product was washed and dried. The yield was 740 kg (96%).

What is claimed is:

1. A process for the preparation of N-acetoacetyl-2,5-dimethoxy-4-chloroanilide which comprises suspending 2,5-dimethoxy-4-chloroaniline in water and adding at least one molar equivalent of diketene at the beginning of the reaction, said reaction being conducted at at temperature not in excess of 50° C.

2. A process as claimed in claim 1, wherein 1.05 to 1.5 mol of diketene per mol of said aniline are added.

3. A process as claimed in claim 1, wherein the aqueous reaction mixture contains an acid.

4. A process as claimed in claim 3, wherein per mol of said aniline 0.1 to 1 mol of acid are added.

5. A process as claimed in claim 3, wherein the acid is acetic acid.

6. A process as claimed in claim 1, wherein the aqueous reaction mixture contains a surfactant.

7. A process as claimed in claim 6, wherein the surfactant is anionic.

8. A process as claimed in claim 1, wherein the starting temperature is 0 to 30° C.

* * * * *